United States Patent
Dartevelle

(10) Patent No.: US 9,339,388 B2
(45) Date of Patent: May 17, 2016

(54) OSTEOSYNTHESIS IMPLANT

(75) Inventor: Philippe Dartevelle, Sermaise (FR)

(73) Assignee: ASSOCIATION MARIE LANNELONGUE, Le Plessis Robinson (FR)

( * ) Notice: Subject to any disclaimer, the term of this patent is extended or adjusted under 35 U.S.C. 154(b) by 0 days.

(21) Appl. No.: 14/119,427

(22) PCT Filed: May 23, 2012

(86) PCT No.: PCT/EP2012/059633
§ 371 (c)(1),
(2), (4) Date: Feb. 27, 2014

(87) PCT Pub. No.: WO2012/160109
PCT Pub. Date: Nov. 29, 2012

(65) Prior Publication Data
US 2014/0163691 A1   Jun. 12, 2014

(30) Foreign Application Priority Data
May 23, 2011   (FR) ...................................... 11 01596

(51) Int. Cl.
*A61F 2/28* (2006.01)
*A61B 17/80* (2006.01)
*A61B 17/02* (2006.01)
*A61B 17/00* (2006.01)
*A61B 17/82* (2006.01)

(52) U.S. Cl.
CPC .............. *A61F 2/28* (2013.01); *A61B 17/8076* (2013.01); *A61B 17/0206* (2013.01); *A61B 17/823* (2013.01); *A61B 2017/00004* (2013.01)

(58) Field of Classification Search
CPC .. A61F 2/28; A61B 17/8076; A61B 17/8028; A61B 17/8085; A61B 17/80

USPC .............. 623/23.45, 23.47; 606/324, 60, 320, 606/280
See application file for complete search history.

(56) References Cited

U.S. PATENT DOCUMENTS

| | | | | |
|---|---|---|---|---|
| 2,486,303 A * | 10/1949 | Longfellow | .................... | 606/71 |
| 3,463,148 A * | 8/1969 | Treace | .......................... | 606/286 |
| 4,327,715 A * | 5/1982 | Corvisier | .......... | A61B 17/8076 |
| | | | | 606/71 |
| 4,599,086 A * | 7/1986 | Doty | ........................... | 606/86 A |
| 4,726,356 A | 2/1988 | Santilli et al. | | |
| 5,087,259 A * | 2/1992 | Krenkel | .......................... | 606/60 |
| 5,092,889 A * | 3/1992 | Campbell, Jr. | ......... | A61B 17/68 |
| | | | | 606/71 |
| 5,261,908 A * | 11/1993 | Campbell, Jr. | ................ | 606/279 |
| 5,571,105 A * | 11/1996 | Gundolf | ................ | A61B 17/82 |
| | | | | 24/21 |
| 5,611,354 A | 3/1997 | Alleyne | | |
| 5,672,177 A * | 9/1997 | Seldin | ............................. | 606/71 |
| 5,827,286 A * | 10/1998 | Incavo | .............. | A61B 17/8009 |
| | | | | 606/282 |

(Continued)

FOREIGN PATENT DOCUMENTS

FR            2 353 274 A1   12/1977

*Primary Examiner* — Alvin Stewart
(74) *Attorney, Agent, or Firm* — Blakely Sokoloff Taylor & Zafman LLP

(57) ABSTRACT

The invention relates to an osteosynthesis implant (1) for adapting the shape and the working volume of a ribcage with a view to the implantation of an artificial heart in said ribcage, characterized in that it comprises the following elements: —a main part (10) which has a shape and dimensions that can be adapted to the shape and the dimensions of the rib cage, —attaching elements (20) for attaching the main part to the ribcage, wherein said attaching elements (20) are rigidly attached to the main part (10), and—a protection (30) for the artificial heart, attached to the main part (10).

26 Claims, 2 Drawing Sheets

(56) References Cited

U.S. PATENT DOCUMENTS

| | | | | |
|---|---|---|---|---|
| 5,941,881 A * | 8/1999 | Barnes | A61B 17/8004 | 606/207 |
| 5,972,006 A * | 10/1999 | Sciaino, Jr. | A61B 17/823 | 606/139 |
| 6,007,538 A * | 12/1999 | Levin | A61B 17/8076 | 606/282 |
| 6,024,759 A * | 2/2000 | Nuss et al. | | 606/237 |
| 6,051,007 A * | 4/2000 | Hogendijk | A61B 17/08 | 606/151 |
| 6,488,685 B1 * | 12/2002 | Manderson | A61B 17/80 | 606/280 |
| 6,540,769 B1 * | 4/2003 | Miller, III | A61B 17/823 | 24/372 |
| 6,572,617 B1 * | 6/2003 | Senegas | | 606/263 |
| 6,918,910 B2 * | 7/2005 | Smith et al. | | 606/60 |
| 7,135,024 B2 * | 11/2006 | Cook et al. | | 606/279 |
| 7,189,237 B2 * | 3/2007 | Huebner | | 606/291 |
| 7,635,365 B2 * | 12/2009 | Ellis | A61B 17/8076 | 606/71 |
| 7,695,501 B2 * | 4/2010 | Ellis et al. | | 606/281 |
| 8,105,366 B2 * | 1/2012 | Null et al. | | 606/280 |
| 8,632,573 B2 * | 1/2014 | Ellis et al. | | 606/280 |
| 8,728,133 B2 * | 5/2014 | Fell et al. | | 606/320 |
| 8,740,903 B2 * | 6/2014 | Bottlang | A61B 17/72 | 606/283 |
| 8,795,342 B2 * | 8/2014 | Reisberg | A61B 17/8076 | 606/101 |
| 8,956,392 B2 * | 2/2015 | Khatchadourian et al. | | 606/279 |
| 9,237,910 B2 * | 1/2016 | Seykora | A61B 17/8076 | |
| 9,265,543 B2 * | 2/2016 | Gephart | A61B 17/8076 | |
| 2002/0128653 A1 * | 9/2002 | Haidukewych | | 606/69 |
| 2003/0125740 A1 * | 7/2003 | Khanna | | 606/61 |
| 2004/0111161 A1 * | 6/2004 | Trieu | | 623/17.16 |
| 2004/0117016 A1 * | 6/2004 | Abramson | A61B 17/8076 | 623/16.11 |
| 2004/0153067 A1 * | 8/2004 | Smith | A61B 17/8076 | 606/60 |
| 2005/0096657 A1 * | 5/2005 | Autericque et al. | | 606/69 |
| 2005/0234448 A1 * | 10/2005 | McCarthy | | 606/57 |
| 2005/0267475 A1 * | 12/2005 | Miller, III | A61B 17/823 | 606/324 |
| 2006/0276896 A1 * | 12/2006 | Fallin et al. | | 623/16.11 |
| 2007/0239161 A1 * | 10/2007 | Giger | A61B 17/8076 | 606/86 A |
| 2007/0270803 A1 * | 11/2007 | Giger | A61B 17/8076 | 606/60 |
| 2008/0082101 A1 * | 4/2008 | Reisberg | | 606/60 |
| 2009/0018587 A1 * | 1/2009 | Bottlang | | 606/280 |
| 2009/0198277 A1 * | 8/2009 | Gordon | A61B 17/688 | 606/248 |
| 2009/0275945 A1 * | 11/2009 | Makower | A61B 17/58 | 606/60 |
| 2009/0312758 A1 * | 12/2009 | Petit et al. | | 606/60 |
| 2010/0004697 A1 * | 1/2010 | Fortin | A61B 17/66 | 606/86 R |
| 2010/0094428 A1 * | 4/2010 | Ralph et al. | | 623/17.19 |
| 2010/0256691 A1 * | 10/2010 | Park | | 606/330 |
| 2010/0331892 A1 * | 12/2010 | Fell et al. | | 606/286 |
| 2012/0296440 A1 * | 11/2012 | Choux et al. | | 623/23.52 |
| 2013/0090695 A1 * | 4/2013 | Bernstein | A61B 17/808 | 606/281 |
| 2013/0304067 A1 * | 11/2013 | Hess | A61B 17/8009 | 606/71 |
| 2014/0135853 A1 * | 5/2014 | Reisberg | | 606/324 |
| 2014/0172020 A1 * | 6/2014 | Gonzalez-Hernandez | | 606/281 |
| 2014/0172116 A1 * | 6/2014 | Maxson et al. | | 623/23.53 |
| 2015/0119887 A1 * | 4/2015 | May | A61B 17/15 | 606/71 |
| 2015/0196396 A1 * | 7/2015 | Thomas | A61B 17/707 | 623/23.47 |
| 2015/0209093 A1 * | 7/2015 | Dallis | A61B 17/8023 | 606/281 |

\* cited by examiner

OSTEOSYNTHESIS IMPLANT

The invention relates in general to the field of cardiac surgery, and more particularly implanting an artificial heart into a live body.

An artificial heart is a prosthesis made from synthetic and/or biological materials, used in treating people having irreversible cardiac failure.

The prosthesis can be a provisional artificial heart, such as for example the heart developed by the company JARVIK, during a wait for cardiac transplant.

It can also be a complete artificial heart. The prosthesis completely replaces the biological heart. Reference can be made for example to an artificial heart made of biosynthetic materials proposed by the company CARMAT, which comprises a portable part (power supply), an implantable part (the cardiac prosthesis and its electrical connection to the portable part) and external products which enable electric power supply of the prosthesis and follow-up on the patient.

However, despite current technological advances, the volume of these models of artificial hearts is greater than the average volume of a biological heart. For example, a heart such as the artificial heart proposed by the company CARMAT can be implanted in the rib cage of some 30% of men and around 70% of women without counting those people having congenital anomalies or anomalies acquired from the thoracic wall) due to lack of space in the rib cage. This artificial heart is however currently known as being the smallest model made to date.

The use of artificial hearts is therefore limited according to the form and dimensions of the rib cage of patients.

Document FR 2 353 274 discloses a costal splint capable of modifying the form of a rib cage. The splint for this comprises a central body and feet for attachment to the rib cage. The central part of the splint also has a local enlargement adapter for receiving and holding an immobilisation wire for connecting the splint and the subjacent wall. However, this device allows modification of a rib cage only, and is not adapted to allow implanting of an artificial heart into a rib cage having insufficient working volume. The same applies for the implant described in document U.S. Pat. No. 4,327,715, the structure of which allows only modification of a rib cage of a patient.

Document U.S. Pat. No. 5,611,354 also discloses heart protections adapted to limit post-operative adhesion formations between adjacent tissue, especially between the heart and the sternum of a patient. However, this protection is provided to protect the natural human heart following surgery, and not an artificial heart. The artificial heart and the natural heart have different form and dimensions. Also, the use of such protection does not however allow implanting of the artificial heart into the rib cage when the working volume of the latter is insufficient.

Finally, document U.S. Pat. No. 4,726,356 describes a cardiovascular retractor whereof the function is to guarantee a surgeon access to the heart of a patient, comprising means adapted to be fixed to the rib cage of the patient to hold the latter open during surgery. The retractor is then removed so the patient can be closed up without the form of the rib cage having been modified.

An aim of the invention is therefore to allow implanting of an artificial heart into a rib cage of a patient, irrespective of the form and dimensions of the rib cage of the patient.

For this, the invention proposes an osteosynthesis implant for adaptation of the form and working volume of a rib cage in light of the to of an artificial heart in said rib cage, characterised in that it comprises the following elements:

a principal part of form and dimensions adaptable to the form and dimensions of the rib cage, attaching elements of the principal part to the rib cage, said attaching elements being fixed solidly to the principal part, and a protection of the artificial heart, fixed on the principal part.

Some preferred, though non-limiting, aspects of the osteosynthesis implant according to the invention are the following:

the principal part is a rod made of an easy-to-model material;

all or part of the implant is made of titanium;

the form of the protection of the artificial heart is adapted to the form of the part of the artificial heart opposite which said protection is arranged;

the protection is a shell made of titanium or a Vicryl plate;

the protection also comprises engagement means with the principal part;

the engagement means are brackets;

the engagement means are a projection, said projection extending from the protection and being adapted to cooperate with a complementary recess made in the principal part, or a recess, said recess being made in the protection and being adapted to cooperate with a projection complementary extending from the protection;

the implant also comprises a reinforcement;

the reinforcement is constituted by the protection;

the implant also comprising suspension means of the artificial heart relative to the implant; and the suspension means are constituted by the protection.

According to a second aspect, the invention propose the use of an osteosynthesis implant in the implanting of an artificial heart into a rib cage of a patient, characterised in that the implant comprises the following elements:

a principal part of form and dimensions adaptable to the form and dimensions of the rib cage, and attaching elements of the principal part to the rib cage, said attaching elements being fixed solidly to the principal part.

According to a final aspect, the invention proposes an implant process of an artificial heart in a rib cage of a patient, comprising the following steps:

removing the biological heart from the patient, implanting the artificial heart, defining a part of the rib cage to be resected as a function of the volume and form of the artificial heart and rib cage, resecting the part of the rib cage now defined, replacing the resected part of the rib cage by an osteosynthesis implant to boost the working volume of said rib cage, and closing the patient up.

Some preferred, though non-limiting, aspects of the implant process are the following:

the form and/or the dimensions of the osteosynthesis implant are adapted as a function of the form and dimensions of the resected part of the rib cage and the artificial heart prior to replacement of the resected part by the osteosynthesis implant;

the adaptation of the form of the osteosynthesis implant is made by curving and/or twisting its principal part;

the protection is also fixed on the principal part of the osteosynthesis implant prior to replacement of the resected part of the rib cage by the osteosynthesis implant;

the protection is fitted with brackets, and the process also comprises a step during which the protection is fixed by insertion of the principal part in said brackets;

all or part of the sternum and/or part of the left ribs from the fourth to the eighth is resected; and the attaching elements are fixed to one of the elements of: ribs, costal cartilage and/or a sternum.

Other characteristics, aims and advantages of the present invention will emerge from the following detailed description with respect to the attached figures, given by way of non-limiting examples and in which.

Figure 3:
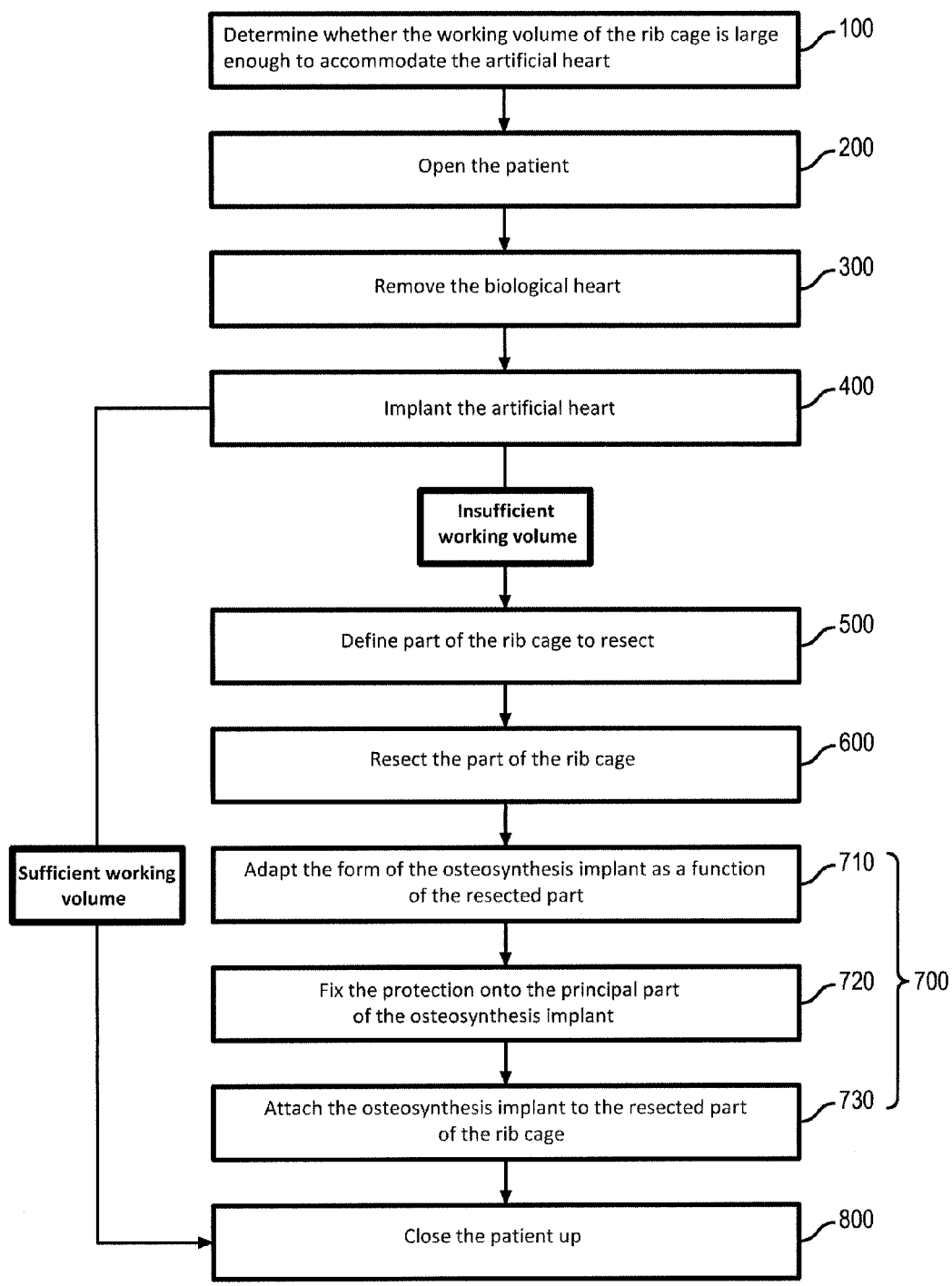
FIG. 3 is an organigram illustrating a different step of an embodiment of an implant process of an artificial heart by means of an implant of the invention.

An implant process of an artificial heart in the rib cage of a patient according to the invention will now be described (see especially FIG. 3 attached).

During such an operation, a surgeon determines first (step 100), as a function of the dimensions and form of the artificial heart and of the rib cage of the patient, whether the working volume of the rib cage of the patient is large enough to receive the artificial heart. Working volume here means the volume of the rib cage capable of taking up the artificial heart. In fact, according to the form of the rib cage, it is understood that the volume of the latter can be considerable without it being possible to implant the artificial heart without risk of damaging the organs of the patient, his/her rib cage and/or the artificial heart. And, as the volume of an artificial heart is generally greater than the average volume of a biological heart, the risks of not being able to directly implant the artificial heart into the rib cage are substantial.

This step 100 can be done before surgery, by scanner examination of the thorax and/or external examination of the patient, then confirmed during surgery, after opening of the rib cage of the patient and replacement of the biological heart by an artificial heart.

Two hypotheses are presented:

either the working volume of the rib cage is sufficient, that is, the form and dimensions of the rib cage are adapted to implanting of the artificial heart: after implanting of the artificial heart into the rib cage (steps 200 to 400), according to conventional surgical techniques not explained in detail here, the surgeon directly closes up the rib cage.

or the working volume of the rib cage is too small, that is, the form and/or dimensions of the rib cage are not appropriate to receive the artificial heart: given that it is currently not possible to reduce the size of the artificial heart, the surgeon therefore has to expand the working volume of the rib cage so he can close it up after implanting of the prosthesis (steps 500 to 700).

For this, the process proposes locally modifying the form of the rib cage to then expand its working volume, by resecting (step 600) part of the rib cage and replacing (step 700) the resected part by reinforcement means whereof the dimensions and form are adapted to both replace the resected part of the rib cage, by increasing the working volume of the latter to allow the artificial heart to be taken up, and to maintain resistance of the rib cage by as best as possible avoiding the risk of infections.

Accordingly, during a first step, (step 600) part of the rib cage is resected.

Since the aim is to increase the place in the rib cage intended to receive the thoracic heart, (step 500) the part to be resected is determined as a function of the initial form of the rib cage, the position of the artificial heart in the rib cage and the form and volume of the artificial heart.

For example, all or part of the sternum and part of the left ribs from the fourth to the eighth can be resected.

In the case of a man of average size presenting an anomaly in the thoracic wall of pectus excavatum, carinatum or arcuatum type, a substantial part of the anterior thoracic wall can be resected.

The rib cage of the patient is opened locally.

During a second step, an osteosynthesis implant 1 is fixed at the level of the resected ribs, adapted to rigidify the rib cage (which has been made fragile by partial resection) and increase its working volume (step 700).

The osteosynthesis implant 1 is modulable, that is, its dimensions and forms can be adapted to the space created during partial resection of the rib cage. For this, the osteosynthesis implant 1 can for example be made as per the description of document US 2008/0082101.

In general, such an implant 1 comprises especially a rod 10 fitted at the level of its ends with attaching elements 20 to the rib cage.

The rod 10 and the attaching elements 20 are made from material compatible with surrounding tissue and resisting corrosion by air and the biological environment.

Also, the material(s) constituting the rod 10 are selected to allow its deformation by folding and torsion, and therefore its adaptation to the space created during resection so that it can be fixed to the rib cage and increase the working volume, and have form memory after modelling to hold the rib cage en position after the implant 1 is placed in (step 710). Titanium, and secondarily steel, are for example materials which can be used together for the rod and the connection means.

The length of the rod 10 can also be adapted to the dimensions in this case created by resection so as to harmoniously reconstruct the rib cage while boosting its working volume. Document US 2008/0082101 proposes for example cutting part of the rod 10 to the preferred length before fixing the attaching elements 20 thereto.

Finally, the attaching elements 20 can be oriented relative to the rod 10 to allow better adaptation of the implant 1 to the rib cage of the patient. These can be pincers, bolts, wires or plates, etc.

In this embodiment, the form and the dimensions of the rod 10 of the osteosynthesis implant 1 are therefore adapted as a function of the volume of the rib cage to be achieved, the initial form of the rib cage and the space freed up following the initial resection step. For this, it is possible, as described in document US 2008/0082101 to adapt the length of the rod, give it a different form by folding (for example by applying one or more curves), and/or twist it locally (see for example FIG. 2). For example, a rod 10 having a curved form whereof the radius of curvature is greater than the initial radius of curvature of the resected part of the rib cage finally increases the working volume of the rib cage.

The attaching elements 20 of the osteosynthesis implant 1 are then positioned and fixed relative to the rod 10.

Finally, the attaching elements 20 of the osteosynthesis implant 1 are fixed to the rib cage (step 730).

The fastening points of the attaching elements 20 on the rib cage depend of course on the parts which have been resected. However, these are generally ribs or costal cartilage. Optionally, in the event where the entire sternum has not been resected, the attaching elements 20 can also be fixed to the sternum by penetration.

Also, according to the dimensions and initial form of the rib cage of the patient, it can prove necessary to put in place more than one osteosynthesis implant 1. An osteosynthesis implant 1 can for example be fixed on the (partially) resected rib, or even an implant 1 on two ribs. So, in the example given above, as many as four implants can be put in place.

It is evident of course that other embodiments of osteosynthesis implants 1 such as that described in document US 2008/0082101 can be used here, insofar as they fulfil the conditions of adaptation to the rib cage to harmoniously reshape the latter following the first step of resection, rigidification of the rib cage following implanting, and adaptation of the working volume of the latter.

The use of an osteosynthesis implant according to the invention therefore harmoniously increases the working volume of the rib cage of the patient by adaptation of its form and its dimensions.

Figure 1:
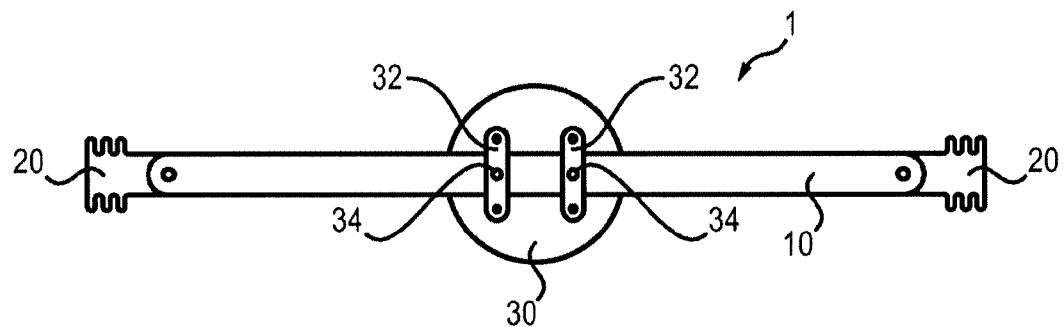
FIG. 1 illustrates a frontal view of an osteosynthesis implant according to the present invention.
Figure 2:
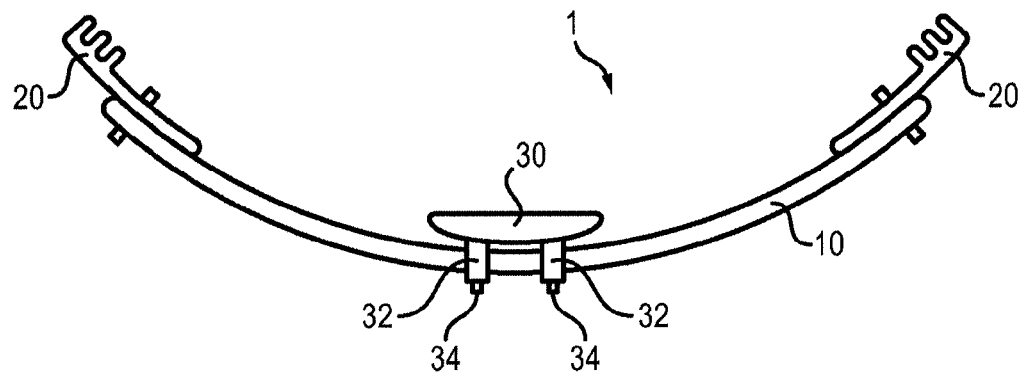
FIG. 2 illustrates a plan view of FIG. 1.

The osteosynthesis implant 1 can also comprise a protection 30 adapted to protect the artificial heart (see FIGS. 1 and 2). The protection 30 can especially be constituted by a shell, whereof the form and dimensions correspond substantially to the form and dimensions of the part of the artificial heart opposite the osteosynthesis implant 1 when the implant 1 is affixed to the rib cage. For example, the shell 30 can have a general concave form, and where appropriate comprise additional recesses and protuberances for improving the correspondence of form with the part of the artificial heart located opposite. It can for example be made by moulding.

By way of variant, the protection 30 can comprise a Vicryl plate.

The protection 30 can be made of the same material as the rest of the osteosynthesis implant, specifically titanium or for example plastic material.

It is then fixed on the implant 1 when being attached to the rib cage (step 720). For this, the protection 30 can for example comprise, at the level of the face opposite the face intended to be opposite the artificial heart, engagement means 32 with the rod(s) of the implant(s), fastening the protection element on the rod(s) 10 of the implant(s) after conformation of the latter and keeping it in position.

Such engagement means 32 can especially be one or more brackets in which the rod(s) 10 of the implant(s) can be slid. The protection 30 also comprises a system 34 adapted to block it in position on the implant 1.

As a variant, the engagement means 32 can also comprise an assembly constituted by at least one projection, fixed on one of the protection 30 and the rod(s) 10 of the implant(s) (not shown in the figures), and adapted to cooperate by friction and/or snap-locking with a corresponding recess made in the other of the protection 30 and the rod(s) 10 of the implant (s).

In the event where more than one osteosynthesis implant 1 is implanted, it is also possible to add a reinforcement adapted especially to prevent the different implants 1 from shifting relative to each other. The role of the reinforcement can also be played by the protection 30 itself.

Finally, the osteosynthesis implant 1 can also comprise suspension means of the artificial heart in the body of the patient. In fact, current artificial hearts are often heavier than biological hearts such that they risk contaminating internal elements of the body, especially veins, during sudden movement or even when the patient is stretched out.

The role of the suspension means can be played by the protection 30, fitted with a fastening system adapted to attach to the artificial heart and keep it in position relative to the rod.

As a variant, the holding means can be a fastening system separate from the protection, such as one or more arms.

Then, during a final step 800, the patient is closed back up according to conventional techniques which will not be described here.

Of course, the present invention is not limited to the embodiments described hereinabove and shown in the diagrams, though the expert cannot make numerous variants and modifications thereto.

The invention claimed is:

1. An osteosynthesis implant for the adaptation of the form and working volume of a rib cage with a view to implanting of an artificial heart into said rib cage, comprising the following elements:
   a principal part of form and dimensions adaptable to the form and dimensions of the rib cage,
   attaching elements of the principal part to the rib cage, said attaching elements being fixed solidly to the principal part, and
   a protection of the artificial heart, fixed on the principal part, wherein said protection includes engagement means configured to fasten the protection to the principal part, wherein the form of the protection of the artificial heart is adapted to the form of the part of the artificial heart opposite which said protection is arranged.

2. The osteosynthesis implant according to claim 1, wherein the principal part is a rod made in easy-to-model material.

3. The osteosynthesis implant according to claim 1, wherein all or part of the implant is made of titanium.

4. The osteosynthesis implant according to claim 1, wherein the protection is a shell made of titanium.

5. The osteosynthesis implant according to claim 1, wherein the protection is a Vicryl plate.

6. The osteosynthesis implant according to claim 1, wherein the engagement means are brackets.

7. The osteosynthesis implant according to claim 1, wherein the engagement means are a projection, said projection extending from the protection and being adapted to cooperate with a complementary recess made in the principal part, or a recess, said recess being made in the protection and being adapted to cooperate with a complementary projection extending from the protection.

8. The osteosynthesis implant according to claim 1, also comprising a reinforcement.

9. The osteosynthesis implant according to claim 8, wherein the reinforcement is constituted by the protection.

10. The osteosynthesis implant according to claim 1, further comprising a suspension means for the artificial heart.

11. The osteosynthesis implant according to claim 10, wherein the suspension means are constituted by the protection.

12. An osteosynthesis implant for the adaptation of the form and working volume of a rib cage with a view to implanting of an artificial heart into said rib cage, comprising the following elements:
    a principal part of form and dimensions adaptable to the form and dimensions of the rib cage,
    attaching elements of the principal part to the rib cage, said attaching elements being fixed solidly to the principal part, and
    a protection of the artificial heart, fixed on the principal part, wherein said protection includes engagement means configured to fasten the protection to the principal part, wherein the protection is a Vicryl plate.

13. The osteosynthesis implant according to claim 12, wherein the principal part is a rod made of an easy-to-model material.

14. The osteosynthesis implant according to claim 12, wherein part of the implant is made of titanium.

15. The osteosynthesis implant according to claim 12, wherein the form of the protection of the artificial heart is adapted to the form of the part of the artificial heart opposite which said protection is arranged.

16. The osteosynthesis implant according to claim 12, wherein the protection also comprises engagement means with the principal part.

17. The osteosynthesis implant according to claim 16, wherein the engagement means are brackets.

18. The osteosynthesis implant according to claim 12, also comprising a reinforcement.

19. The osteosynthesis implant according to claim 12, also comprising suspension means of the artificial heart relative to the implant.

20. An osteosynthesis implant for the adaptation of the form and working volume of a rib cage with a view to implanting of an artificial heart into said rib cage, characterised in that it comprises the following elements:
   a principal part of form and dimensions adaptable to the form and dimensions of the rib cage,
   attaching elements of the principal part to the rib cage, said attaching elements being fixed solidly to the principal part, and
   a protection of the artificial heart, fixed on the principal part, wherein said protection includes engagement means configured to fasten the protection to the principal part, wherein the protection also comprises engagement means with the principal part, wherein said engagement means are a projection, said projection extending from the protection and being adapted to cooperate with a complementary recess made in the principal part, or a recess, said recess being made in the protection and being adapted to cooperate with a complementary projection extending from the protection.

21. The osteosynthesis implant according to claim 20, wherein the principal part is a rod made of an easy-to-model material.

22. The osteosynthesis implant according to claim 20, wherein part of the implant is made of titanium.

23. The osteosynthesis implant according to claim 20, wherein the form of the protection of the artificial heart is adapted to the form of the part of the artificial heart opposite which said protection is arranged.

24. The osteosynthesis implant according to claim 20, wherein the protection is a shell made of titanium.

25. The osteosynthesis implant according to claim 20, also comprising a reinforcement.

26. The osteosynthesis implant according to claim 20, also comprising suspension means of the artificial heart relative to the implant.

* * * * *